(12) United States Patent
Meier et al.

(10) Patent No.: US 8,945,863 B2
(45) Date of Patent: *Feb. 3, 2015

(54) METHOD FOR MEASURING THE ACTIVITY OF CATHEPSIN B AFTER DE-INHIBITION

(75) Inventors: Hans Jörg Meier, Constance (DE); Hans Werner Hofer, Constance (DE)

(73) Assignee: Papst Licensing GmbH & Co. KG, St. Georgen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/143,704

(22) PCT Filed: Jan. 8, 2010

(86) PCT No.: PCT/DE2010/000011
§ 371 (c)(1),
(2), (4) Date: Sep. 23, 2011

(87) PCT Pub. No.: WO2010/078868
PCT Pub. Date: Jul. 15, 2010

(65) Prior Publication Data
US 2012/0015389 A1    Jan. 19, 2012

(30) Foreign Application Priority Data
Jan. 8, 2009 (DE) .................... 10 2009 004 371

(51) Int. Cl.
*C12Q 1/37* (2006.01)
(52) U.S. Cl.
USPC .......................................................... 435/23
(58) Field of Classification Search
USPC ....................................................... 435/4, 23
See application file for complete search history.

(56) References Cited

U.S. PATENT DOCUMENTS

| | | | |
|---|---|---|---|
| 4,215,563 A | 8/1980 | Clardy et al. | |
| 4,243,753 A | 1/1981 | Regnier et al. | |
| 4,668,630 A | 5/1987 | Louderback | |
| 4,762,617 A | 8/1988 | Stevens | |
| 4,840,730 A | 6/1989 | Saxena | |
| 5,336,412 A | 8/1994 | Huse et al. | |
| 5,935,846 A | 8/1999 | Schumacher et al. | |
| 5,973,110 A | 10/1999 | Muller et al. | |
| 6,171,851 B1 | 1/2001 | Schumacher et al. | |
| 7,112,453 B2* | 9/2006 | Hutchens et al. | 436/525 |
| 2001/0034057 A1 | 10/2001 | Schumacher et al. | |
| 2003/0087426 A1* | 5/2003 | Schumacher et al. | 435/288.6 |
| 2003/0186345 A1 | 10/2003 | Hortin | |
| 2005/0153306 A1* | 7/2005 | Harris et al. | 435/6 |
| 2008/0059687 A1 | 3/2008 | Mayer et al. | |
| 2009/0275051 A1 | 11/2009 | Niles et al. | |
| 2010/0267054 A1* | 10/2010 | Hofer et al. | 435/7.4 |

FOREIGN PATENT DOCUMENTS

| | | |
|---|---|---|
| DE | 102007034120 A1 | 3/2008 |
| DE | 102007017681 A1 | 1/2009 |
| DE | 102007057388 A1 | 5/2009 |
| EP | 0 329 190 A2 | 8/1989 |
| EP | 0 776 374 B1 | 12/2009 |
| WO | 9700969 A1 | 1/1997 |
| WO | 98/37226 A1 | 8/1998 |
| WO | 2005070546 A1 | 8/2005 |
| WO | 2009006877 A2 | 1/2009 |

OTHER PUBLICATIONS

Wei Guo, et al., Crosslinked mercerized cellulose membranes for the affinity chromatography of papain inhibtors, Journal of Membrane Science, (2002), pp. 53-62, 197, Buffalo, New York.
International Search Report for PCT/DE2010/000011 filed Jun. 1, 2010.
Written Opinion for PCT/DE2010/000011 filed Jan. 8, 2010.
Heidrun Kirschke et al., "Activity of lysosomal cysteine proteinase during differentiation of rat skeletal muscle," Biochem. J., 1983, vol. 214, pp. 871-877.
M. Koohmaraie et al., "Comparisons of Four Methods for Quantification of Lysosomal Cysteine Proteinase Activities," J. Anim. Sci., 1990, vol. 68, pp. 2362-2370.
Irmgard Assfalg-Machleidt et al., "Cathepsin B—Indicator for the Release of Lysosomal Cysteine Proteinases in Severe Trauma and Inflammation," Biological Chemistry Hoppe-Seyler, vol. 317 Supplement Issue, May 1990, pp. 211-222.
J. Rozman-Pungerčar et al., "Inhibition of Papain-like Cysteine Proteases and Legumain by Caspase-specific Inhibitors: When Reaction Mechanism is More Important than Specificity," Cell Death and Differentiation, 2003, vol. 10, pp. 881-888.
Maciej Siewiński et al., "A Comparison of Cysteine Peptidase Activity and their Inhibitors in the Blood Serum of Pregnant Women," Pakistan J. Medical Science, 2004, vol. 20, No. 4, pp. 381-384.
Charlotte Kopitz et al., "Reduction of Experimental Human Fibrosarcoma Lung Metastasis in Mice by Adenovirus-Mediated Cystatin C Overexpression in the Host," Cancer Research, Oct. 1, 2005, vol. 65, No. 19, pp. 8608-8612.

(Continued)

*Primary Examiner* — Ralph Gitomer
(74) *Attorney, Agent, or Firm* — Fitch, Even, Tabin & Flannery, LLP

(57) ABSTRACT

The present invention relates to a method for measuring the activity of enzymes in a sample which contains at least one enzyme and at least one enzyme inhibitor corresponding to said enzyme, whereby after de-inhibition the activity of the released enzyme is measured in such a way that a substrate is added to the sample and the time course of the concentration of at least one reaction product (cleavage product) is recorded and the enzyme specific substrate has a fluorogenic part which is cleaved in the enzymatic reaction and the fluorescence (measuring parameter) of which can be detected in a wavelength range where the measuring parameter can be assigned unambiguously to the enzyme activity to be measured, whereby the de-inhibition is carried out by immersing a rigid carrier, to which the inhibitor binding substance is bound, into the sample. The present invention relates also to a corresponding device for measuring the activity on enzymes in a sample.

14 Claims, 3 Drawing Sheets

(56) References Cited

OTHER PUBLICATIONS

Eugene R. Bissell et al., "Synthesis and Chemistry of 7-Amino-4-(trifluoromethyl)coumarin and Its Amino Acid and Peptide Derivatives," Journal of Organic Chemistry, 1980, vol. 45, No. 12, pp. 2283-2287.

S. W. Cox et al., "Detection of Cathepsin B- and L-, elastase-, tryptase-, trypsin-, and dipeptidyl peptidase IV-like activities in crevicular fluid from gingivitis and periodontitis patients with peptidyl derivatives of 7-amino-4-trifluoromethyl coumarin," J. Periodontal Research, Nov. 1989, vol. 24, No. 6, pp. 353-361.

Elzbieta Skrzydlewska et al., "Evaluation of serum cathepsin B and D in relation to clinicopathological staging of colorectal cancer," World Journal of Gastroenterology, 2005, vol. 11, No. 27, pp. 4225-4229.

Wojciech Kielan et al., "Evaluation of changes in the activity of proteolytic enzymes and their inhibitors in the processes that accompany the growth of gastric cancer," Gastric Cancer, 2004, vol. 7, pp. 17-23.

Jos W. J. Van Der Stappen et al., "Activation of Cathepsin B, Secreted by a Colorectal Cancer Cell Line Requires Low pH and is Mediated by Cathepsin D," International Journal of Cancer, 1996, vol. 67, pp. 547-554.

Lukas Mach et al., "Maturation of Human Procathepsin B," The Journal of Biological Chemistry, Apr. 29, 1994, vol. 269, No. 17, pp. 13030-13035.

Jerica Rozman et al., "Autocatalytic processing of recombinant human procathepsin B is a bimolecular process," Federation of European Biochemical Societies Letters 459, FEBS 22741, 1999, pp. 358-362.

John S. Mort et al., "Molecules in Focus, Cathepsin B," International Journal of Biochemistry & Cell Biology, 1997, vol. 29, No. 5, pp. 715-720.

PCT International Search Report dated Oct. 17, 2011 for International Application No. PCT/EP2011/061138, 4 pages.

PCT International Preliminary Report on Patentability and Written Opinion of the International Searching Authority (English Translation) dated Jan. 8, 2013 for International Application No. PCT/EP2011/061138, 11 pages.

Barry R. Rifkin et al., "Cathepsin B and L Activities in Isolated Osteoclasts," Biochemical and Biophysical Research Communications, Aug. 30, 1991, vol. 179, No. 1, pp. 63-69.

* cited by examiner

METHOD FOR MEASURING THE ACTIVITY OF CATHEPSIN B AFTER DE-INHIBITION

This is a national phase application of international application PCT/DE2010/000011, filed Jan. 8, 2010, claiming priority to German Patent Application No. 10 2009 004 371.3, filed Jan. 8, 2009, the content of which is fully incorporated by reference herein.

The present invention relates to a method and a device for measuring the activity of enzymes after de-inhibition, particularly of proteolytic enzymes, mainly of cysteine proteinases which may be important for the diagnosis and therapy of malignant tumours.

In a sample there are enzyme inhibitor complexes, and the activity of the proteolytic enzymes are in vivo mainly inhibited by binding of inhibitors. A similar topic is described in WO97/00969.

Additionally the German patent application 10 2007 017 681.5 relates to a similar invention and also the German patent applications 10 2007 057 388.1 and 10 2007 034 120.7 the complete disclosure of which is referred to.

According to this state of art the measurement of the activity of such enzymes is known which are mainly inhibited in the sample by inhibitors and the activities of which can be measured in such a way that at first the sample is passed through a flow through column where the inhibitors inhibiting the enzyme will be removed from the sample. Afterwards the inhibitor-free enzyme is added to a measuring vessel where after adding of a suitable substrate the activity of the enzyme will be measured, e. g. by means of the increase of the concentration of at least one cleavage product during the reaction time.

The purpose of the present patent application is to provide a method and a device for measuring the activity of enzymes after de-inhibition which achieves a substantial increase in sensitivity and greater reliability of the measurements so that a surgical intervention is no longer necessary in order to get the biological sample because serum can now be used instead as biological sample.

Furthermore the present invention provides a method and a device for measuring the activity of enzymes after de-inhibition which for the daily routine of doctor's practice or for small scale medical laboratories or also in emergency cases along with rather simple handling offers sufficiently exact and particularly cost-effective results which serve as a prognostic factor (in case of therapeutic decisions) or as a marker (for diagnostic purposes).

This purpose is accomplished by means of the method for measuring the activity of enzymes after de-inhibition according to claim 1 and by means of the device for measuring the activity of enzymes after de-inhibition according to claim 10.

Further embodiments and additions arise from the subclaims.

In case of measuring the activity of enzymes by means of de-inhibition fluorogenic substrates turned out to be advantageous where 7-amino-4-methylcoumarine serves as a fluorogenic substance bound to the C-terminus of an oligopeptide, preferentially to a dipeptide, the N-terminus of which is protected by a carboxybenzyl protecting group (abbreviation: Cbz or Z).

However, in some cases the unambiguousness, that is the precision of the measuring results, is not sufficient.

By using 7-amino-4-trifluoromethylcoumarine as C-terminus instead of 7-amino-4-methyl-coumarine the emission spectrum of the cleaved fluorogenic substance is shifted to longer wavelengths so that the fluorescence of the cleaved fluorogenic substance can be detected in a wavelength range, where other luminescent substances of the sample to be measured do not disturb the measuring result any longer so that a higher sensitivity of the measurement of the activity of such enzymes can be achieved, particularly with generic devices and methods.

If the biological sample is for example a tissue sample or a tissue homogenate, then by using a bypass the portion of the enzyme activity of e.g. the cysteine protease can be measured after passing the sample through the bypass which is originally not inhibited in the sample. It is known that in tissue homogenates not all the protease, which is to be measured, is inhibited, but only a part of it. Thus, out of two activity measurements, that is, after passage of the biological sample through the affinity chromatography column and through the bypass the difference of these two values provides the activity of the enzyme originally inhibited in the biological sample.

Due to the present invention fluorescence emission can be measured in such cases in a wavelength range of about 500 nm and more The following figures are shown:

In FIG. 1 and FIG. 2 module A is shown in a planar sectional drawing and module B is shown in a spatial representation In the description of figures, identical reference codes are used for identical or functionally identical elements.

Figure 1:
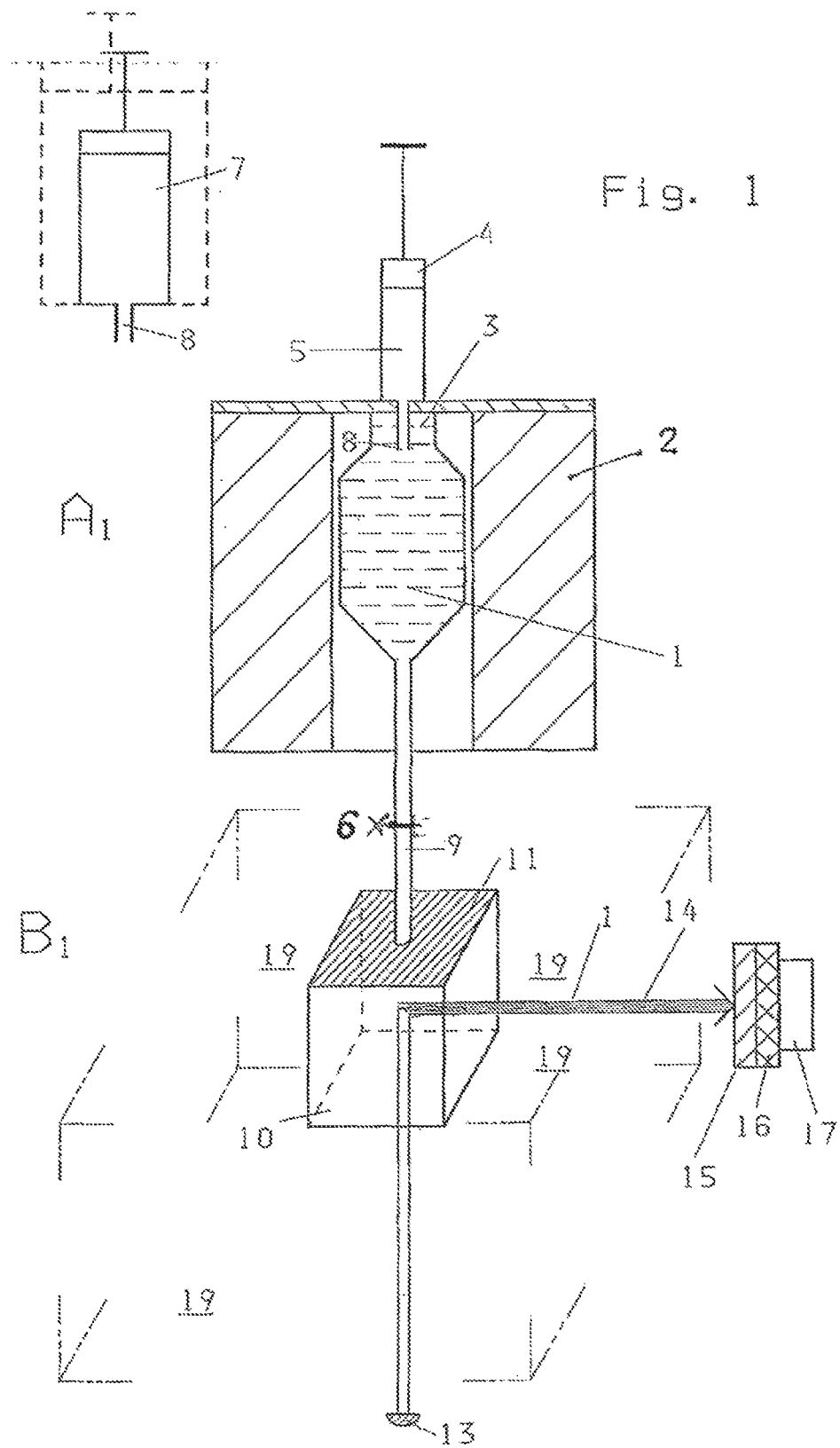
FIG. 1 shows a device for measuring the activity of enzymes after de-inhibition according to a first embodiment of the present invention.

There an exchangeable affinity chromatography column 1 is enclosed by a thermostat 2 which has at least one Peltier element. The column 1 essentially consists of a cylinder filled with a porous substance, a carrier, which functions as a gel, to which a substance is bound that binds the inhibitor of the enzyme inhibitor complex tighter than the enzyme does. Thus the enzyme is set free for measuring its activity. Into the upper opening 3 of the column 1, to the lower end of which advantageously a locking valve 6 is affixed, the tip 8 of an exchangeable syringe 4 extends, which contains in a volume 5 the sample together with the enzyme inhibitor complex.

The volume 5 becomes virtually zero when the syringe 4 is pressed out, and the content is discharged into the column 1, in which is a carrier (preferably compactly packed).

An elution buffer of a volume being ca. $100$-$10^3$ times the sample volume will then be added totally or partially into the column 1 by means of a second syringe 7.

A first procedure is as follows: the sample will be incubated together with a part of the elution buffer in the column 1 at a well defined temperature (e. g., ca. 4° C.) for a certain time, in practice ca. 10-18 min. In particular 15 min turned out to be effective. Afterwards through of a further addition of elution buffer by means of the syringe 7 the free enzyme is eluted and the eluted solution flows downwards into module B according to FIG. 1 when the locking valve 6 is opened.

In the first procedure initially the valve 6 is open until the column buffer partially entered the column 1 or until the sample is distributed in the length of the column. Up to this time a volume, which is not taken into account in the measurement can be discharged (e. g., as described in FIG. 2 via the drain 28). After the incubation time this valve 6 will be opened for elution, and afterwards shut so that a residual volume does not worsen the measurement value. This residual volume may be discharged also via the drain 28.

In a second alternative procedure the sample flows together with the added column buffer downwards through the column with a velocity which secures that in this manner the inhibitor of all enzyme inhibitor complexes of the sample is transferred to the immobilised substance in the column which binds the inhibitor tighter than the enzyme does. This is a quasi-migration incubation. Thus, the free enzyme is eluted and the eluted solution flows downward into the module B according to FIG. 1.

In this procedure in the beginning also a volume will be discharged (as described in FIG. 2 via drain 28); the same happens after the quasi optimal measurement volume has passed.

Thus, module A of FIG. 1 is a device for de-inhibition which substantially is located over the measuring box module B, whereby the volume discharged from the column 1 is discharged into module B according to FIG. 1 by means of a pipe or tube through a cover plate 11 into a fluorescence cuvette 10. (The cover plate is blackened so as to absorb the laser light passing through the measuring sample). The free enzyme cleaves as a proteolytic enzyme according to the enzyme assay from the substrate added into the cuvette 10 a fragment which fluoresces in its free form. From the time course of the increasing fluorescence intensity the enzyme activity of the released enzyme can be determined at a well defined temperature (which is adjusted by means of the Peltier elements 19). In the lower measuring box (module B) there is a laser diode 13 for exciting this fluorescence. The laser diode usefully emits light of the wavelength which corresponds to the excitation maximum of the fluorescing substrate fragment. The emitting fluorescence light 14 is detected orthogonally to the laser beam direction by means of a photo diode 17. The edge filter 15 and the interference filter 16 filter almost all scattered light of the exciting light and secure that only fluorescence light comes to the photo diode 17.

The temperature control of the affinity chromatography column 1 in module A is adjusted at 3-20° C., preferably at 4-5° C., as along with binding the inhibitor to the affinity chromatographic material in the column the proteolytic enzyme is released and may digest itself, i. e. at higher temperatures one proteolytic enzyme molecule attacks another enzyme molecule.

The measurement of the enzyme activity in module B is carried out at the controlled temperature of 37° C. (for human medical purposes), (for this purpose an additional device may be used so as to control the temperature also by means of Peltier elements: thermostat 19). However the activity may also be measured at 20° C. or at ambient temperature, but each selected temperature must be kept constant during the whole measuring time.

In the most elementary case the cuvette 10 is also embodied as disposable. (It may be filled in the beginning with measuring buffer and the ingredients according to the enzyme assay). However, the addition of this mixture may be carried out in a direct manner into the cuvette 10, or owing to circumstances via the channel 9 by means of an additional valve and pump, and if necessary, also an appropriate measuring buffer may be added. After completing the elution the enzymatic reaction is started by adding substrate. This may be carried out, e. g., as shown in FIG. 2, from a substrate container 18 via the valve 26, or as shown in FIG. 1 may be added via a syringe (not shown) through the cover plate 11.

The components 1, 5, 4, 10 may be embodied as cheap disposables. The advantage of the exchangeable components is that no parts of a sample of one patient come in contact with those of another patient! One has to consider that the body fluid of one patient is given to the column 1 as a sample and mainly the enzyme inhibitor remains in the column during the elution; however, it is not clear whether also other components remain in the column. In any case, the sample in the fluorescence cuvette 10 does not only contain the free enzyme but also most of the other components of the original body fluid. A further advantage of this concept is that complex mechanical components such as valves/pumps are not necessary.

The dilution of the eluate with measuring buffer may be advantageous for a good measuring result, may be that it is necessary. The combination of a laser diode and/or photo diode positioned close to the measuring cuvette leads to a high detection limit.

Figure 2:
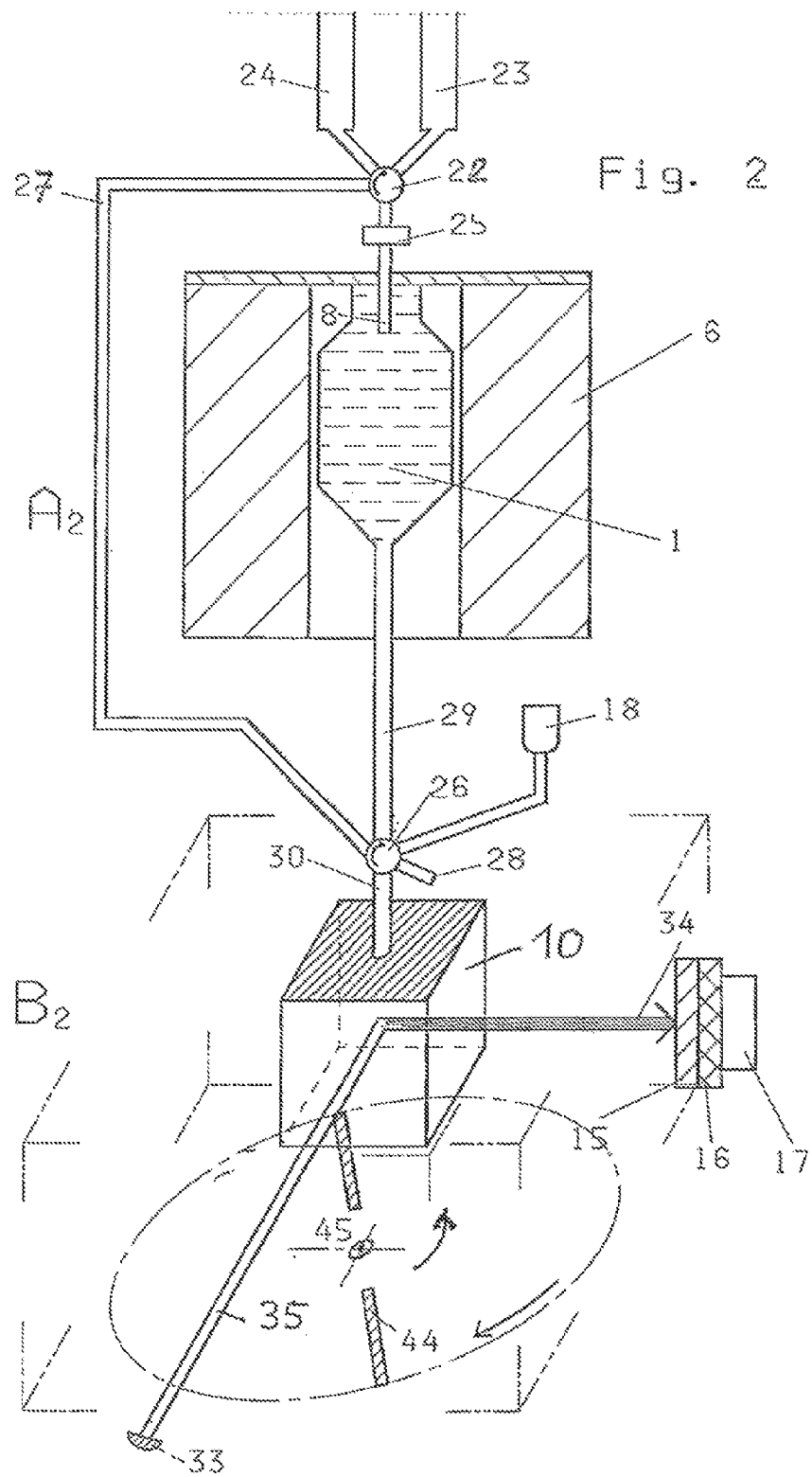
FIG. 2 shows a device with an advanced function compared to that of FIG. 1 being a quasi semi-automatable device

FIG. 2 shows a device being functionally advanced compared to FIG. 1 and being quasi half-automatable, however the column 1 may be operated as in FIG. 1 in both of the methods. Therefore at the upper and lower end of the column 1 multi-way valves 22, 26 are provided. Components of that device may also be combined with an arrangement of FIG. 1.

FIG. 2 has also an affinity chromatography column 1 which is enclosed by a temperature controlled unit 6 (e. g., Peltier element) and preferably adjusted at 4° C. The column is compactly packed with a material to which a substance is bound which has a higher affinity to the inhibitors than an enzyme inhibitor complex of the sample being of interest, e. g., the substance bound to the packed material Sepharose gel is papain, and the sample contains e. g. the enzyme inhibitor complex of cathepsin B. After the input of the sample from a container through a tube 23 via a valve 22 (characterized by a rotating arrow) a column buffer from the inlet 24 will be fed into the column 1, whereby the valve 22 is switched.

The tube 23 may be a disposable or/and serves as inlet from a container which may be used for further measurements. The channel 24 may be embodied as a further disposable second syringe made of plastics and having a distinct volume which in general is a multiple of the volume of the sample, or it may simply be a column buffer reservoir or it may lead to such a reservoir, whereby in the corresponding position of the valve 22 to the inlet of the column 1 the intake-flow for the column buffer will be unblocked.

The pump 25 is arranged downstream after the valve 22 so as to create, if necessary, any pressure (also p=0) for an optimal flow through the column. The position of the valve 22 may also be adjusted in such manner that the sample and/or the column buffer is passed through a bypass 27 to the lower outlet of the flow through column 1 or to the valve 26. At the outlet of the column 1 this additional valve 26 is provided (also indicated by means of a rotating arrow) for a following additional purpose: when the sample flows through the column 1, a first portion of a volume will be disposed via the outlet 28. Then the turning valve is turned to the flow through direction 30 toward the measuring box B, because the further volume is more suitable for an exact measurement. The rest of the eluted fluid will then disposed again via the outlet 28.

In order to determine the amount of the disposed volume the dilution of the sample will be determined after passing through the column 1. Perhaps a simple device should be provided for determination of the volume, which is disposed via the channel 28, and with this value the volume of the eluted sample containing the free enzyme can be determined as a difference to the volume of the elution buffer fed in via 24.

After passing through the channel 30 into a vessel 10 (e. g., cube-shaped or cuboid-shaped) the sample whose enzyme is released from inhibitors flows into the vessel 10 which beforehand was filled with measuring buffer and ingredients according to the enzyme assay. In order to start the enzyme reaction the optimal amount of substrate is added from the reservoir 18.

The vessel 10 may also be a disposable for simple requirements whereby the cube 10 may be made of plastics, for example.

It may be a fluorescence cuvette, whereby in the module B a laser diode 33 with an emitting wavelength of λ=400 nm is provided.

This laser beam from 33 is about orthogonal to the falling direction, i. e. about 90° to the direction of the flow direction via channel 29 or 30. Perpendicular to that (as viewed by the observer in an angle of 90° to the right) a fluorescence light beam 34 is shown which is emitted by the cleavage product and falls on an edge filter 15 and on an interference filter 16 arranged plan-parallel to 15, and then on a photo diode 17 also arranged plan-parallel to 15 and able at its output to measure the intensity of the fluorescence radiation (as in FIG. 1). Thus, the beams 34, 35 lie in a plane which is preferably perpendicular to the falling direction. That is substantially a detection of the fluorescence emission according to the off-axis procedure.

Below the fluorescence cuvette 10 a magnetic stirrer 44 is indicated rotating around the axis 45 so as to homogenize the mixture as well as possible. Fluorescence is emitted immediately after the particles of the sample get into contact with the substrate, its intensity is proportional to the concentration of the cleavage product and this is a proportional measure of the enzyme activity.

Figure 4:
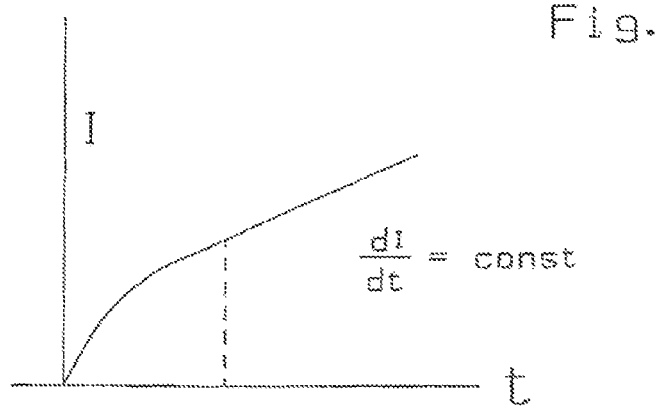
FIG. 4 illustrates the emitted fluorescence intensity versus time.

The measurement curve for the emitted fluorescence intensity in FIG. 4 changes into a straight line after an initial stage, and as soon as the course of the graph is a straight line, its slope is measured so as to get the desired result dI/dt. FIG. 4 is representative for all other figures.

In the most elementary case module A is a disposable chromatographic column, into the upper end of which a first disposable syringe containing the sample is introduced and afterwards a second syringe containing column buffer; its outlet 9 may be directly connected via the valve 6 to the measuring box 10, whereby this may also be a prepared cheap disposable (as already described). Module B, in any case the measuring box 10, is to be temperature controlled, and therefore adjacent to and around the measuring box 10 a further Peltier element 16 is provided. (It must be preferably adjusted to 37° C. for human medical purposes). Thus, alternatively a substrate reservoir 18 may be provided with a direct channel to box 10. Preferably, however, the feeding goes from the substrate reservoir to box 10 indirectly via the channel 9 or 29 or 30.

In the most elementary case module B is a cheap disposable filled with measuring buffer and further ingredients such as e. g., a non-ionic surfactant and dithiothreitol or cysteine.

The valve is indispensable if the sample is eluted from the column by means of the flow through method, because in this case a first portion of the eluate will be disposed. It is also indispensable if the sample is incubated on the column for some time; for this purpose after charging the column with the sample a certain amount of column buffer has to be fed into the column and an equivalent portion has to be discharged from the outlet of the column; in this way the sample seeps into the column and all the enzyme inhibitor complexes of the sample virtually get into contact with the substance being immobilised on the column and able to bind the inhibitor more tightly.

While in the arrangement according to FIG. 1 the laser beam 14 and the emitted and detected fluorescence light go parallel to or in the drawing plane or section plane of module A, these beams 34, 35 lie in FIG. 2 in a plane being perpendicular to the section plane of module A, i. e. generally perpendicular to the falling direction or flow through direction in module A (detection of the fluorescence emission according to the off-axis method).

Thus, below the measuring cuvette 10 or module B a mixer for homogenising the content of the cuvette 10 is well located in this place and advantageously arranged for simple handling, e. g. as a magnetic stirrer 44, 45.

A further embodiment according to the present invention is as follows: a porous substance, a carrier to which the inhibitor-binding substance is bound and which in turn binds the inhibitor of the enzyme-inhibitor complex tighter than the enzyme does can surprisingly be substituted by a cellulose strip to which the inhibitor-binding substance can be bound in an adsorptive or covalent manner, preferably covalently. In case of a covalent binding it turned out to be particularly advantageous to carry out the last step of the binding procedure photochemically.

A covalent binding of papain to cellulose is carried out in three steps:
1. Activation of the free OH-groups of cellulose, e. g. by means of periodate.
2. Coupling of a bifunctional reagent to the activated cellulose.
3. Reaction with papain.

In the first step a round filter having a diameter of 110 mm is treated with periodate. The second reaction step is carried out with the heterobifunctional reagent p-azidobenzoylhydrazide (ABH). The phenyl azido group can be used after photoactivation for covalent coupling to CH- and NH-groups in proteins which are activated by hydrogen bridges. Thus, in the third step the ABH-treated round filter is put on a long wave (310 nm) UV light source and before irradiation covered with a papain containing solution, this procedure is carried out with both sides of the filter.

The efficiency of coupling of papain to cellulose was measured by means of a fluorometric activity test using Arg-Arg-AMC as substrate and compared with the activity of papain on papain-agarose (250 μg/ml gel).

Thus the filter was divided into 32 segments of about the same size, one segment having an area of about 3 cm$^2$.

The following mean values (n=3) were found:

| material | carrier [mg] | rel. fluorescence intensity (netto) | papain [μg] |
|---|---|---|---|
| papain-cellulose | 18 | 1454 | 16.9 |
| papain-agarose | 1.2 | 1076 | 12.5 |

Thus, the cellulose segments and the agarose used for the cathepsin B test contained comparable amounts of papain.

Three different sera were compared regarding the measurable protease activity by means of Z-Arg-Arg-AFC as substrate before and after treating them with papain which was either immobilised on cellulose filter or on agarose. In this procedure either 50 μl papain-agarose or a 1/32 segment of the above described papain-cellulose were used.

|  | serum 1 | serum 2 | serum 3 |
|---|---|---|---|
| relative fluorescence intensity (serum untreated) | 1835 ± 249 | 1805 ± 50 | 1791 ± 53 |
| rel. fluorescence intensity (serum treated with papain-cellulose) | 3806 | 4702 | 4757 |
| rel. fluorescence intensity (serum treated with papain-agarose) | 3732 | 4995 | 4478 |
| activity (serum treated with papain-cellulose) | 0.44 | 0.65 | 0.66 |
| activity (serum treated with papain-agarose) | 0.42 | 0.71 | 0.60 |

Activities are given in nmol of reacted substrate per minute and per ml of serum. The incubation time was 60 min at 37° C.

At the de-inhibition of the biological sample by means of such a prepared cellulose strip the whole device according to module A (FIG. 1) is not necessary any longer.

Instead, in a simple alternative method of de-inhibition the prepared cellulose strip will be immersed into the biological sample which is already diluted with measuring buffer and is in a temperature controlled reaction vessel. The sample will be brought to a given temperature, preferentially to 20° C., however, any other temperature between 4° C. and 20° C. can be chosen. After de-inhibition which is, for example at 20° C., accomplished after 5 min the cellulose strip will be removed from the sample and then the activity measurement will be carried out. If the so-called end point detection is used, a portion of the de-inhibited sample will be put into a further temperature controlled reaction vessel which already contains the substrate and the ingredients necessary for the enzyme assay.

In the closed reaction vessel the sample will be incubated at the chosen reaction temperature. After a predetermined time, which is preferentially between 30 and 40 min, the reaction vessel together with the cover will be shaken so as to bring the water condensed on the cover back to the sample. Then the sample will be transferred into the measuring vessel 111 and the fluorescence intensity will be measured. By means of a calibration curve the activity of the de-inhibited enzyme in the sample can then be determined.

Figure 3:
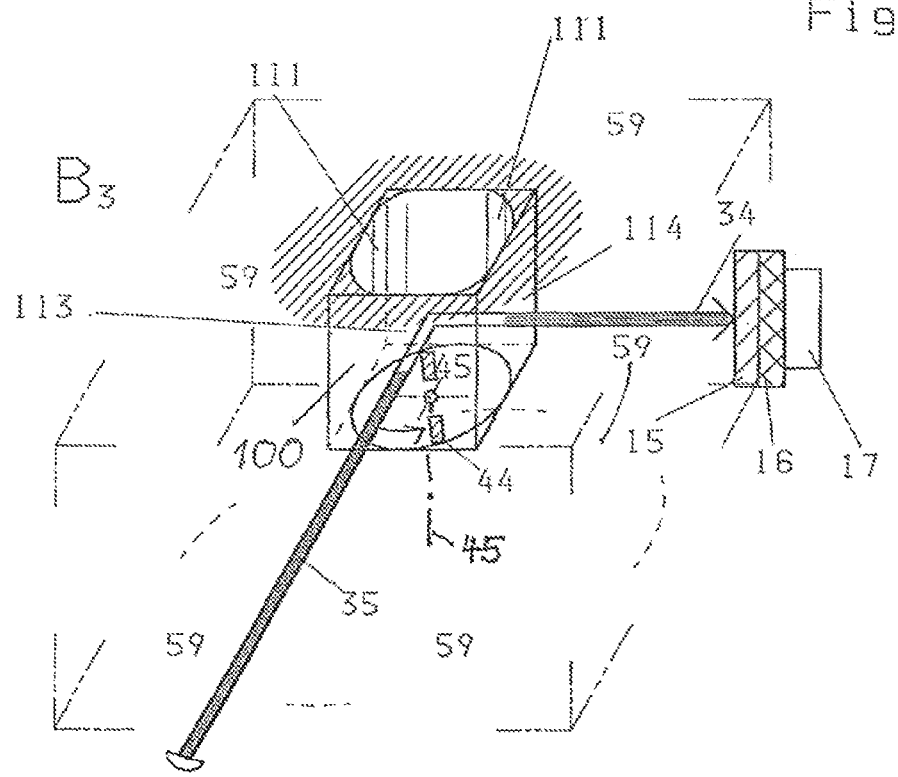
FIG. 3 shows a device for measuring the activity of enzymes after de-inhibition according to a further embodiment of the present invention

The fluorescence emission can be measured as indicated in FIG. 3 according to the off axis method or by means of a small-scale commercial fluorimeter embodied as a handy set which works according to the epifluorescence method or in a microtitre plate by means of a fluorescence reader which works also according to the epifluorescence method.

If the sample is a tissue homogenate, then by measuring the enzyme activity without de-inhibition the activity of the portion of the enzyme can be measured which is not inhibited, and out of the enzyme activity after de-inhibition by means of the prepared cellulose strip the activity of the whole amount of enzyme in the biological sample can be determined and the difference of both values yields the amount of the enzyme which is inhibited in the biological sample.

As an alternative to the cellulose strip a pin made of a porous material as a rigid carrier can be used, for example porous ceramics having a sufficiently large hollow volume to which the inhibitor binding substance is bound in an adsorptive or covalent manner, preferably covalently. In this case the carrier has a sufficient inherent stability as well as a maximum hollow volume together with a corresponding large area of the interior wall.

In the above description for human medical purposes a preferred temperature for measuring the enzyme activity of 37° C. is given. This instruction should, however, not be understood as a strict instruction. Experiments between a measuring temperature of 20° C. and 40° C. result in measuring times between 120 and 20 minutes.

The present invention has been described by means of preferred embodiments, however, it is not limited to them, but in particular results out of to the following claims.

The invention claimed is:

1. A method for measuring activity of cathepsin B in a liquid biological sample being selected from the group consisting of blood plasma and blood serum and containing at least cathepsin B and at least one enzyme inhibitor corresponding to cathepsin B, wherein the enzyme inhibitor blocks enzyme activity of cathepsin B by binding with cathepsin B to form an enzyme-inhibitor complex, the method comprising:
   exposing an inhibitor-binding substance to the biological sample to remove the at least one enzyme inhibitor from the enzyme-inhibitor complex to provide a first sample containing active enzyme cathepsin B, the inhibitor binding substance associated with a de-inhibition device, the de-inhibition device being a rigid carrier configured for immersion into the liquid biological sample and removal therefrom;
   mixing an enzyme specific substrate with the first sample to form a second sample, wherein the enzyme specific substrate includes a di- or oligopeptide with the fluorogenic group 7-Amino-4-trifluoromethylcoumarin (AFC) bound to the C-terminum of the di- or oligopeptide and with a protecting group bound to the N-terminus of the di- or oligopeptide, the fluorogenic group being cleavable during enzymatic reaction with the active enzyme cathepsin B;
   incubating the second sample to effect the enzymatic reaction thereby forming a cleavage product containing the cleaved fluorogenic group; and
   measuring amount of cleavage product produced during the enzymatic reaction using fluorescence as a measuring parameter;
   wherein the fluorescence measuring parameter for the enzyme activity is at a wavelength of at least about 500 nm; and
   wherein the inhibitor-binding substance effects the removal of the at least one enzyme inhibitor from the liquid biological sample with the removal of the de-inhibition device and associated binding substance from the biological sample.

2. The method according to claim 1, wherein the inhibitor-binding substance is covalently bound to the de-inhibition device.

3. The method according to claim 2, wherein the inhibitor-binding substance is covalently bound to the de-inhibition device via a chemical or photochemical procedure.

4. The method according to claim 2, wherein the step of exposing the inhibitor-binding substance to the biological sample is carried out at about 4° C. to about 30° C., wherein the de-inhibition device comprises a cellulose strip, and wherein the de-inhibition device is removed from the first sample prior to addition of the enzyme specific substrate.

5. The method according to claim 4, wherein the step of exposing the inhibitor-binding substance to the biological sample is carried out in a first reaction vessel at a first constant temperature, the step of incubating the second sample is carried out at a second constant temperature in a second reaction vessel, and the step of measuring the amount of cleavage product is carried out at a third constant in a measuring vessel.

6. The method according to claim 5, wherein the fluorescence is measured using an off-axis method.

7. The method according to claim 5, wherein the fluorescence is measured using an epifluorescence method.

8. The method according to claim 1, wherein the protecting group on the N-terminus is carboxybenzyl group (Cbz).

9. The method according to claim 6, wherein the enzyme specific substrate is a dipeptide having the fluorogenic group on its C-terminus and a protecting group on its N-terminus and wherein the fluorogenic group is 7-amino-4-trifluoromethylcoumarin.

10. The method according to claim 7, wherein the protecting group on the N-terminus is carboxybenzyl group (Cbz).

11. The method according to claim 7, wherein the enzyme specific substrate is a dipeptide having the fluorogenic group on its C-terminus and a carboxybenzyl group on its N-terminus and wherein the fluorogenic group is 7-amino-4-trifluoromethylcoumarin.

12. The method according to claim 5, wherein the first and second reaction vessels are temperature controllable.

13. The method according to claim 5, wherein the second reaction vessel is also used as the measuring vessel.

14. A method for measuring enzyme activity in a liquid biological sample containing at least one enzyme and at least one enzyme inhibitor corresponding to the at least one enzyme wherein the enzyme inhibitor blocks enzyme activity by binding with the enzyme to form an enzyme-inhibitor complex, the enzyme being cathepsin B, the liquid biological sample selected from the group consisting of blood plasma and blood serum, the method comprising:

exposing an inhibitor-binding substance to the biological sample to remove the at least one enzyme inhibitor from the enzyme-inhibitor complex to provide a first sample containing active enzyme, the inhibitor binding substance associated with a de-inhibition device, the de-inhibition device being a rigid carrier configured for immersion into the liquid biological sample and removal therefrom;

mixing an enzyme specific substrate with the first sample to form a second sample, wherein the enzyme specific substrate includes a di- or oligopeptide with the fluorogenic group 7-Amino-4-trifluoromethylcoumarin (AFC) bound to the C-terminum of the di- or oligopeptide and with a protecting group bound to the N-terminus of the di- or oligopeptide, the fluorogenic group being cleavable during enzymatic reaction with the active enzyme;

incubating the second sample to effect the enzymatic reaction thereby forming a cleavage product containing the cleaved fluorogenic group; and measuring amount of cleavage product produced during the enzymatic reaction using fluorescence as a measuring parameter;

wherein the fluorescence measuring parameter is at a wavelength of about 500 nm; and wherein removal of the de-inhibition device from the liquid biological sample effects the removal of the at least one enzyme inhibitor from the liquid biological sample.

* * * * *